(12) United States Patent
Andjelic et al.

(10) Patent No.: US 9,044,524 B2
(45) Date of Patent: Jun. 2, 2015

(54) ABSORBABLE POLYETHYLENE DIGLYCOLATE COPOLYMERS TO REDUCE MICROBIAL ADHESION TO MEDICAL DEVICES AND IMPLANTS

(75) Inventors: Sasa Andjelic, Nanuet, NY (US); Joerg Priewe, Kiel (DE)

(73) Assignee: Ethicon, Inc., Somerville, NJ (US)

( * ) Notice: Subject to any disclaimer, the term of this patent is extended or adjusted under 35 U.S.C. 154(b) by 362 days.

(21) Appl. No.: 12/609,101

(22) Filed: Oct. 30, 2009

(65) Prior Publication Data

US 2011/0104227 A1    May 5, 2011

(51) Int. Cl.

| A61L 31/06 | (2006.01) |
|---|---|
| C08G 63/02 | (2006.01) |
| A61L 17/00 | (2006.01) |
| A61L 17/12 | (2006.01) |
| A61L 26/00 | (2006.01) |
| A61L 27/18 | (2006.01) |
| A61L 27/34 | (2006.01) |
| A61L 27/54 | (2006.01) |
| A61L 27/58 | (2006.01) |
| A61L 29/06 | (2006.01) |
| A61L 29/08 | (2006.01) |
| A61L 29/14 | (2006.01) |
| A61L 29/16 | (2006.01) |
| A61L 31/10 | (2006.01) |
| A61L 31/14 | (2006.01) |
| A61L 31/16 | (2006.01) |
| A61K 8/85 | (2006.01) |

(52) U.S. Cl.
CPC .............. *A61L 17/005* (2013.01); *A61L 17/12* (2013.01); *A61L 26/0019* (2013.01); *A61L 26/0066* (2013.01); *A61L 27/18* (2013.01); *A61L 27/34* (2013.01); *A61L 27/54* (2013.01); *A61L 27/58* (2013.01); *A61L 29/06* (2013.01); *A61L 29/085* (2013.01); *A61L 29/148* (2013.01); *A61L 29/16* (2013.01); *A61L 31/06* (2013.01); *A61L 31/10* (2013.01); *A61L 31/148* (2013.01); *A61L 31/16* (2013.01); *A61L 2300/404* (2013.01)

(58) Field of Classification Search
None
See application file for complete search history.

(56) References Cited

U.S. PATENT DOCUMENTS

| 3,942,532 A | 3/1976 | Hunter et al. |
|---|---|---|
| 3,997,512 A | 12/1976 | Casey et al. |
| 4,048,256 A | 9/1977 | Casey et al. |
| 4,076,798 A | 2/1978 | Casey et al. |
| 4,080,969 A | 3/1978 | Casey et al. |
| 4,095,600 A | 6/1978 | Casey et al. |
| 4,118,470 A | 10/1978 | Casey et al. |
| 4,122,129 A | 10/1978 | Casey et al. |
| 4,343,788 A | 8/1982 | Mustachich et al. |
| 4,435,590 A | 3/1984 | Shalaby et al. |
| 4,438,253 A | 3/1984 | Casey et al. |
| 4,452,973 A | 6/1984 | Casey et al. |
| 4,938,763 A | 7/1990 | Dunn et al. |
| 5,442,033 A | 8/1995 | Bezwada |
| 5,464,929 A | 11/1995 | Bezwada et al. |
| 5,599,852 A | 2/1997 | Scopelianos et al. |
| 5,618,552 A | 4/1997 | Bezwada et al. |
| 5,644,002 A * | 7/1997 | Cooper et al. ................ 525/411 |
| 5,653,992 A | 8/1997 | Bezwada et al. |
| 5,688,900 A | 11/1997 | Cooper et al. |
| 5,696,178 A | 12/1997 | Cooper et al. |
| 5,719,256 A | 2/1998 | Tamai et al. |
| 5,728,752 A | 3/1998 | Scopelianos et al. |
| 5,736,589 A | 4/1998 | Cooper et al. |
| 5,824,333 A | 10/1998 | Scopelianos et al. |
| 6,147,168 A | 11/2000 | Jamiolkowski et al. |
| 6,224,894 B1 | 5/2001 | Jamiolkowski et al. |
| 6,355,772 B1 | 3/2002 | Gruber et al. |
| 6,403,655 B1 | 6/2002 | Bezwada |
| 6,514,517 B2 | 2/2003 | Jamiolkowski et al. |
| 6,716,251 B1 | 4/2004 | Asius et al. |
| 6,932,974 B2 | 8/2005 | Bezwada et al. |
| 7,652,127 B2 | 1/2010 | Andjelic |
| 7,754,233 B2 | 7/2010 | Andjelic et al. |
| 7,868,127 B2 | 1/2011 | Andjelic et al. |
| 7,968,656 B2 | 6/2011 | Andjelic et al. |
| 7,977,403 B2 | 7/2011 | Lohrmann et al. |
| 8,440,215 B2 | 5/2013 | Andjelic et al. |
| 8,575,301 B2 | 11/2013 | Andjelic et al. |
| 2002/0132960 A1 | 9/2002 | Haile et al. |
| 2005/0048124 A1 | 3/2005 | Sarangapani |
| 2006/0009839 A1 | 1/2006 | Tan |
| 2006/0051398 A1 * | 3/2006 | Andjelic et al. ............. 424/424 |
| 2006/0263329 A1 * | 11/2006 | Eemeta et al. ............. 424/78.37 |
| 2006/0263330 A1 | 11/2006 | Emeta et al. |

(Continued)

FOREIGN PATENT DOCUMENTS

| CN | 1524903 | 9/2004 |
|---|---|---|
| CN | 1655738 | 8/2005 |

(Continued)

OTHER PUBLICATIONS

Andjelic et al. (Hydrophilic absorbable copolyester exhibiting zero-order drug release, 23 Pharm. Res. 821 (No. 4) (2006), non-patent literature 1 on IDS of Nov. 12, 2009).*
Andjelic, S., et al 'Hydrophilic Absorbable Copolyester Exhibiting Zero-Order Drug Release' Pharmaceutical Research (2006) vol. 23, Issue 4 pp. 821-834.
Andjelic, S., et al 'The Polyoxaesters' Polymer International (2007) vol. 56, Issue 9 pp. 1063-1077.
Ko, H.L. et al 'In vitro and in vivo inhibition of lectin mediated adhesion of *Pseudomonas aeruginosa* by receptor blacking carbohydrates' (1987) vol. 15, Issue 4 pp. 237-240.

(Continued)

*Primary Examiner* — H. Sarah Park

(57) ABSTRACT

The present invention is directed to absorbable polyether esters that have been found to reduce bacterial adhesion to materials such as medical devices and implants. More specifically, the invention is directed to novel amorphous co-polymers comprising polyethylene diglycolate (PEDG) copolymerized with lactide-rich monomers.

13 Claims, 2 Drawing Sheets

(56) References Cited

U.S. PATENT DOCUMENTS

| | | |
|---|---|---|
| 2008/0055086 A1 | 3/2008 | Cantatore et al. |
| 2008/0103284 A1 | 5/2008 | Andjelic |
| 2008/0103285 A1 | 5/2008 | Andjelic et al. |
| 2008/0243101 A1 | 10/2008 | Andjelic et al. |
| 2009/0104276 A1 | 4/2009 | Andjelic et al. |
| 2009/0239786 A1* | 9/2009 | Stopek .............. 514/6 |

FOREIGN PATENT DOCUMENTS

| | | |
|---|---|---|
| EP | 0807653 | 11/1997 |
| EP | 1430916 | 6/2004 |
| EP | 1324783 | 3/2006 |
| EP | 1251794 | 2/2007 |
| EP | 1392198 | 5/2008 |
| JP | 52-147691 | 12/1977 |
| JP | 58-040318 | 3/1983 |
| JP | 59-100130 | 6/1984 |
| JP | 59-100131 | 6/1984 |
| JP | 03-014826 | 1/1991 |
| JP | 08-295730 | 11/1996 |
| JP | 10-045885 | 2/1998 |
| JP | 2008-505728 | 2/2008 |
| JP | 2009-535434 | 10/2009 |
| RU | 95113864 | 7/1997 |
| RU | 2232779 | 7/2004 |
| WO | 00/18821 | 4/2000 |
| WO | 03/043593 | 5/2003 |
| WO | WO 03/099169 | 12/2003 |
| WO | WO 2004/030715 | 4/2004 |
| WO | 2006/125098 | 11/2006 |
| WO | 2006/125099 | 11/2006 |
| WO | 2006/125121 | 11/2006 |
| WO | 2006/125125 | 11/2006 |
| WO | WO2006/125098 | 11/2006 |
| WO | WO 2008/055086 | 3/2008 |
| WO | 2009/042882 | 4/2009 |
| WO | WO 2009/109306 | 9/2009 |

OTHER PUBLICATIONS

Veyries, M-L, et al 'Control of Staphylococcal Adhesion to Polymethylmethacrylate and Enhancement of Susceptibility to Antibiotics and Poloxamer 407' Antimicrob Agents Chemother. (2000) vol. 44, Issue 4 pp. 1093-1096.

International Search Report re: PCT/US2008/077889 dated Jan. 5, 2009.

USPTO Advisory Action dated Feb. 27, 2012 in U.S. Appl. No. 11/864,153.

USPTO Final Rejection dated Oct. 25, 2011 in U.S. Appl. No. 11/864,153.

USPTO Non-Final Rejection dated May 9, 2011 in U.S. Appl. No. 11/864,153.

USPTO Restriction Requirement dated Oct. 28, 2010 in U.S. Appl. No. 11/864,153.

U.S. Appl. No. 11/864,153, filed Sep. 28, 2007.

International Search Report re: PCT/2010/054020 dated Jul. 8, 2011.

Golike, R.C. et al 'Crystallization of copolymers of ethylene glycol and diethylene glycol terephthalate' Journal of Polymer Science Volume 54, Issue 160, pp. 277285, Oct. 1961.

Kawashima, Y. et al 'Preparation of multiple unit hollow microspheres (microballoons) with acrylic resin containing tranilast and their drug release characteristics (in vitro) and floating behavior (in vivo)' Journal of Controlled Release, vol. 16, pp. 279-288 (1991).

Nam, Y.S. et al 'Protein loaded biodegradable microspheres based on Plga-protein bioconjugates' Journal of Microencapsulation, vol. 16, No. 5 pp. 625-637 (1999).

Ouchi, T. et al 'Encapsulation and/or Release Behavior of Bovine Serum Albumin within and from Polylactide-Grafted Dextran Microspheres' Macromolecular Bioscience, vol. 4 pp. 458-463 (2004).

Packhaeuser, C.B. et al 'In situ forming parenteral drug delivery systems: an overview' European Journal of Pharmaceutics and Biopharmaceutics (2004), 58 pp. 445-455.

Patkar, M. et al 'Effect of diethylene glycol (DEG) on the crystallization behavior of poly(ethylene terephthalate) (PET)' Journal of Applied Polymer Science. Volume 47, Issue 10, pp. 1749-1763, 10 Mar. 1993.

Seganov, I. et al 'Effect of Diethylene Glycol Content and Annealing Temperature on the Structure and Properties of Polyethylene Terephthalate)*' Journal of Applied Polymer Science. (1986) vol. 32 pp. 3371-3392.

Vogt, F.G. et al 'Structural Analysis of Polymorphism and Solvation in Tranilast' Journal of Pharmaceutical Sciences, vol. 94, No. 3 pp. 651-665 (2005).

Yu, T. et al 'The effect of units derived from diethylene glycol on crystallization kinetics of poly(ethylene terephthalate)' Die Makromolekulare Chemie Volume 187, Issue 11, pp. 2697-2709, Nov. 1986.

International Search Report dated May 9, 2008 for International Application No. PCT/US2007/082773.

International Search report dated Aug. 31, 2009 for International Application No. PCT/US2009/041280.

* cited by examiner

US 9,044,524 B2

ABSORBABLE POLYETHYLENE DIGLYCOLATE COPOLYMERS TO REDUCE MICROBIAL ADHESION TO MEDICAL DEVICES AND IMPLANTS

FIELD OF THE INVENTION

The present invention is directed to absorbable polyether esters that have been found to reduce bacterial adhesion to materials used as medical devices and implants. More specifically, the invention is directed to novel amorphous co-polymers comprising polyethylene diglycolate (PEDG) copolymerized with lactide-rich monomers capable of forming antimicrobial adhesion barriers.

It has been reported that non-ionic surfactants such Poloxamer 407 or Triton x100 might reduce bacterial attachment to medical implants. Veyries, et al. in "Control of Staphylococcal Adhesion to Polymethylmethacrylate and Enhancement of Susceptibility to Antibiotics by Poloxamer 407", Antimicrobial Agents and Chemotherapy, Vol. 44, No. 4, April 2000, p. 1093-1096, reports of the anti-adhesive effect of Poloxamer 407 on polymethylmethacrylate orthopaedic cements and the further purported effect on antibiotic activity. Additionally, WO 2004030715 discloses compositions for inhibiting attachment of microorganisms to the surface of biomaterials that include a polyether, such as a poloxamer as applied to contact lenses. However, such types of surfactants are limited to certain molecular weights, because they are essentially non-absorbable in humans and not able to find a pathway through the liver or kidney. In addition, these substances are easily displaced from a surface by proteins in the blood.

Also surface modification using polyethylene glycol (PEG) grafting is well known; however, PEG is not absorbable in the human body. Ko et al., in "In Vitro and in Vivo Inhibition of Lectin Mediated Adhesion of *Pseudomonas aeruginosa* by Receptor Blocking Carbohydrates", Inst. Hyg., Cologne, Fed. Rep. Ger. Infection (Munich, Germany) (1987), 15(4), 237-40, describe in vitro and in vivo adhesion of *P. aeruginosa* was mediated by N-acetylneuraminic acid (NANA) receptors. They concluded that blocking of bacterial lectin receptors with specific carbohydrates might be of clinical relevance to prevent bacterial attachment to organ cells. However, the reference does not describe diglycolate-based copolymers to prevent bacterial adhesions. Andjelic et al, in "The Polyoxaesters", Polymer International (2007), 56(9), 1063-1077, describe absorbable polyoxaesters and their semi-crystalline copolymers suitable in a variety of medical applications including lubricious coatings and adhesion prevention. However, the inventors are silent in regards to diglycolate-based copolymers to prevent bacterial adhesions.

US 2006051398 and Andjelic et al. in "Hydrophilic Absorbable Copolyester Exhibiting Zero-Order Drug Release", Pharmaceutical Research (2006), 23(4), 821-834 describe fully amorphous copolymers of poly(ethylene diglycolate) and glycolide as useful in a variety of medical applications. However, the references do not describe lactide-rich diglycolate-based copolymers to prevent bacterial adhesions.

US 2008243101 describes liquid copolymers of poly(ethylene diglycolate) and caprolactone as useful as fillers in plastic surgery applications.

US 2008103284 and US 2008103285 describe semi-crystalline copolymers of poly(ethoxyethylene diglycolate) and glycolide useful in variety of medical applications including fibers, microspheres and melt blown non-woven constructs. However, the references do not describe lactide-rich diglycolate-based copolymers to prevent bacterial adhesions. In summary, the copolymers of poly(ethylene diglycolate) with lactide have not been described in the open or patent literature, nor there is any suggestion of their potential use in antibacterial coating applications.

Surprisingly, it was discovered that a new class of absorbable polymers which are soluble or dispersible in common organic solvents are useful for coating of medical devices and implants to reduce the attachment of bacteria and additionally being useful as a drug releasing system.

SUMMARY OF THE INVENTION

Described herein are compositions comprising an amorphous co-polyester comprising the reaction product of a polycondensation polyester and lactide-rich monomers, wherein the polycondensation polyester comprises the reaction product of diglycolic acid and/or a derivative thereof and ethylene glycol; wherein the co-polyester comprises about 30 to 70% by weight of the polycondensation polyester based on the total weight of the co-polyester and comprises an average molecular weight of about 5,000 to about 30,000 g/mol and is soluble in an organic solvent, most preferably a non-toxic organic solvent. These compositions demonstrate the ability to limit bacterial attachment when used such as a coating for medical devices.

DETAILED DESCRIPTION

Figure 1:
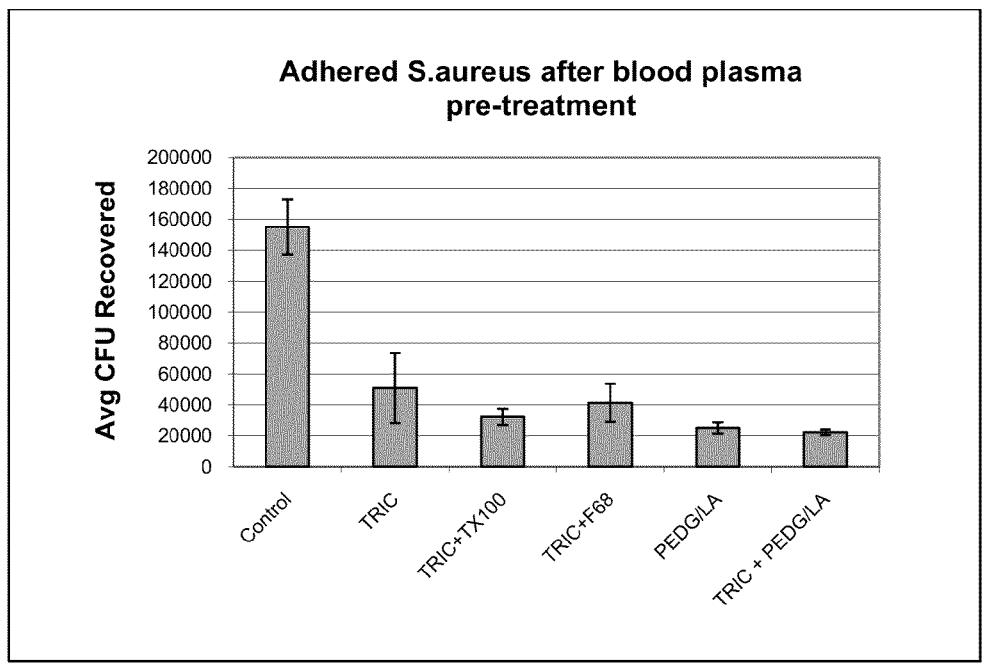
FIG. 1 depicts the anti-adhesion properties of the compositions of this invention in comparison with a control and the control with other polymers coatings in a 20 minute incubation study.

The co-polyester described herein has been found to have the ability to resist microbial adhesion and serve as coatings or films on medical devices or may also comprise the material of which a medical device is made of. The co-polyesters of this invention are fully amorphous which makes them soluble in a variety of organic solvents, which is advantageous for applying the compositions of this invention as coatings or films.

In one embodiment, the co-polyester comprises the reaction product of a polycondensation polymer and a lactide rich composition, wherein the polycondensation polyester comprises the reaction product of diglycolic acid and/or a derivative thereof and ethylene glycol.

In another embodiment, the polycondensation polyester comprises the reaction product of diglycolic acid and/or a derivative thereof, up to about 25 mole percent of an aliphatic diacid based on the total moles of acid, and ethylene glycol. Specifically, the aliphatic diacid may be an aliphatic alpha-omega dicarboxylic acid, including but not limited to 3,6-dioxaoctanedioic acid, 3,6,9-trioxaundecanedioic acid, and combinations thereof.

The polycondensation polyester may be synthesized by conventional techniques using conventional processes. For example, in a condensation polymerization, diglycolic acid and ethylene glycol may be polymerized in the presence of a catalyst at elevated temperatures and reduced pressures. A variety of catalysts may be used, but organometallic compounds have been found to be useful. The catalyst for the polycondensation step of the synthesis is preferably tin based, e.g., stannous octoate. The most desirable catalyst is dibutyltin oxide and is present in the diglycolic acid/ethylene glycol monomer mixture at a sufficiently effective molar ratio of monomer to catalyst, e.g., ranging from about 5,000/1 to about 100,000/1. For example, the ratio of 10,000/1 has been found to be quite suitable. The reaction is typically carried out at a temperature range from about 100° C. to about 220° C., preferably from about 140° C. to about 200° C., under an inert atmosphere until esterification of diglycolic acid is complete. Preferably, 180° C. has been found to be a desirable reaction temperature when employing a vertically stirred reactor. It should be noted that the optimum reaction temperature may be reactor and catalyst level dependent but can be found by one having only ordinary skill through the use of experiments. The first stage of the polycondensation reaction (inert gas at atmospheric pressure) is followed by polymerization under reduced pressure until the desired molecular weight and viscosity are achieved.

The weight average molecular weight of the polycondensation polymer can range from about 2,000 to about 10,000 g/mol, preferably from about 4,000 to about 7,000 g/mol, most preferably about 5,000 g/mol. This corresponds to an inherent viscosity range from about 0.20 to about 0.40 dL/g.

When the molecular weight of the polycondensation polymer is lower than about 2,000 g/mol, the molecular weight of the final co-polyester is too low to achieve the desired mechanical properties necessary for many medical device applications. We have found, in general, that a molecular weight of the polycondensation polymer greater than about 10,000 g/mol, is not necessary to achieve desirable properties. One could however envision that this value is not an absolute bar. One might for instance, increase the molecular weight of the polycondensation polymer, and lower the amount of the lactide component used in the preparation of the final co-polyester.

The amount of polycondensation polyester used to prepare the co-polyester is about 30 to 70% by weight based on the total weight of the co-polyester.

As used herein, the term "lactide rich" composition describes compositions that comprise more than 50 weight %, preferably from about 80 to about 100 weight %, most preferably 100 weight % lactide (l, d, dl, meso) monomers. Other constituents of the lactide rich composition may include, but are not limited to, glycolides, p-dioxanones, trimethylene carbonates, tetramethylene carbonate, epsilon-caprolactone, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one, and combinations of two or more thereof. The preferred lactone monomer is lactide (l, d, dl, meso).

In another embodiment, the co-polyester may comprise the reaction product of a polycondensation polyester and two or more lactones. For example, the co-polyester may comprise the reaction product of the polycondensation polyester, at least 50 mole percent lactide based on the total moles of lactone, and a second lactone monomer.

The co-polyesters of the present invention may be conveniently synthesized by reaction of a dihydroxy poly(alkylene diglycolate) homopolymer or copolymer with a lactide rich composition by conventional techniques using conventional processes. For example, the polycondensation polyester is used as an α,ω-dihydroxy macroinitiator in a subsequent ring opening polymerization (ROP) with a lactide or a lactone mixture. The lactone monomers are copolymerized into the polycondensation polyester in the presence of a conventional organometallic catalyst at elevated temperatures. The catalyst for the ROP may be already present as residual catalyst in the polycondensation polyester or may be additional catalyst added in this second step of the synthesis. A suitable catalyst added at the time of the ROP can be an organometallic catalyst. The ring-opening organometallic catalyst is preferably tin based, e.g., stannous octoate, and is present in a sufficiently effective amount in the monomer mixture, preferably at a molar ratio of lactone monomer-to-catalyst ranging from about 20,000/1 to infinity (i.e. no additional catalyst used). Thus one might utilize a tin-IV compound such as dibutyltin oxide at a diacid, for instance, diglycolic acid-to-catalyst ratio of about 10,000/1 to prepare the polycondensation polyester and then add a tin-II compound such as stannous octoate at a lactone-to-added-catalyst molar ratio of about 240,000/1 at the time of the ring opening polymerization. The co-polyesters of the present invention may be synthesized alternately with no additional catalyst being added at the time of the ROP.

The ROP step can be immediately conducted in the same reactor as that used to synthesize the polycondensation polyester immediately after the completion of the polycondensation step, if the reactor can provide adequate heat transfer and agitation. The lactide or lactone mixture can be added as a solid, a slurry, or in molten form. Alternately, the ROP can be conducted in a separate reactor at a later date, or in the reactor used for the polycondensation polyester at a later date. If this is the case, the polycondensation polyester is discharged from its reactor and is stored in an environment that minimizes water pick up and hydrolysis. In the case of adding lactide monomer, the monomer can be added as a solid. The reactor is closed and the pressure reduced. The reactor is usually held under vacuum for a prolonged period of time, for instance overnight, to allow drying. Nitrogen is then introduced into the reactor to bring the pressure to slightly greater than one atmosphere, and the purge cycle repeated for a total of three times. The temperature of the reaction mass is brought up to 130° C. Once at this temperature, the agitator is activated. The temperature is then increased to 150° C. to complete the mixing. This mixing step is essential to produce the co-polyesters of the present invention as inadequate mixing tends to allow the formation of homopolymeric sequences which can then crystallize to an extent greater than optimum. To ensure that reactants are fully mixed, in-situ spectroscopic probes (such as Near-Infrared) can be conveniently used. If additional catalyst is to be added, it is typically added once the batch has been completely mixed. The temperature is quickly brought up to the final reaction temperature, with 190° C. being a most preferred temperature, and held there for typically 4-5 hours. The exact reaction conditions will depend on the catalyst and its level; final reaction temperatures can vary from about 180° C. to 220° C., and more preferably from about 190° C. to about 200° C. Reaction times can vary from about 90 minutes to several hours, depending on the catalyst and it level, and is typically conducted until the desired conversion of monomer to polymer is achieved.

An alternate reaction scheme that has been employed to prepare the co-polyesters of the invention has involved adding the lactide or lactone mixture as a molten stream into the reactor. Thus the polycondensation polyester is added first, typically as a molten stream and the reactor evacuated. The reactor is heated to 150° C. Molten lactide (or other lactide rich mixture) at a temperature of about 135° C. is added to the reactor. Although the batch temperature drops slightly, it is quickly brought back up to 150° C. at which point mixing is started. At this point, the process that was described above is followed.

Under the above described conditions, the co-polyesters of polycondensation polyester and lactide, will typically have a weight average molecular weight of about 5,000 g/mol (a.k.a. Daltons) to about 30,000 g/mol, preferably about 10,000 g/mol to about 20,000 g/mol, and more preferably about 12,000 g/mol to about 16,000 g/mol. These molecular weights are sufficient to provide an effective inherent viscosity, typically between about 0.20 to about 0.5 deciliters per gram (dL/g), preferably about 0.30 to about 0.40 dL/g as measured in a 0.1 g/dL solution of hexafluoroisopropanol (HFIP) at 25° C.

The co-polyesters of this invention are fully amorphous and soluble in a variety of organic solvents (readily soluble in acetone) and may be applied directly to an medical device by means of coating or may comprise the material that the device is made of, such as a resorbable suture, tissue fastener or wound healing dressings. The term "readily soluble", as used herein, is intended mean that the compositions of this invention are easily soluble in organic solvents without the need to raise the temperature or adjust the pH of the solvent.

For example ultra-thin film coatings of the material of current invention can be applied on mesh, films or sutures. Once applied, the coatings are useful in the reducing the attachment of bacteria on its surface.

Suitable solvents for applying the compositions of this invention to substrates may include but not limited to ethyl acetate, acetone, toluene, hexane, benzene, diethyl ether, chloroform, methylene chloride, tetrahydrofuran, acetonitrile, ethyl lactate, N-methylpyrolidone and benzyl alcohol, or mixtures thereof. However, preferred organic solvents are those that are non-toxic. As used herein, the term "non-toxic" means any non-chlorinated and/or non-carcinogenic organic solvents that have a permissible exposure limit (PEL) of 100 mg/m$^3$ (i.e., based on the Occupational Safety and Health Administration's (OSHA) 8-hour time-weighted average (TWA) concentration (see, for example, 29 CFR 1910.1000, Table Z-1). Exemplary non-toxic solvents include but are not limited to methanol, ethanol, 2-propanol, ethyl acetate, butyl acetate, 2-ethoxy ethyl acetate, acetone, methyl ethyl ketone (MEK), toluene, and xylene, with the most preferred being ethanol, 2-propanol, ethyl acetate, acetone, and methyl ethyl ketone (MEK).

Alternatively, articles such as medical devices may be molded from the co-polyester described herein by various conventional injection and extrusion molding processes and used directly in a body. For example, the co-polyester may be molded to form films then sterilized by ethylene oxide, gamma or e-beam sterilization (i.e. between 15 to 40 kGy). Alternatively, the co-polyester may be a component of a medical device, i.e., the co-polyester may form one layer of a multi-laminate hernia repair mesh, or may be suspended in a polymer solution and coated onto at least a portion of a medical device.

In one embodiment, the present invention relates to a composition comprising an absorbable copolyester of a polycondensation polyester and lactide, more specifically, an absorbable copolyester comprising the reaction product of poly (ethylene-co-ethoxyethylene diglycolate) (PEDG-21) and lactide, where the copolyester comprises about 30 to 70% by weight of the poly(ethylene-co-ethoxyethylene diglycolate) based on the total weight of the copolyester. Polycondensation polyester comprises the reaction product of diglycolic acid and/or a derivative thereof with ethylene glycol and diethylene glycol, wherein ethylene glycol is predominate component in the diol mixture.

Poly(ethylene-co-ethoxyethylene diglycolate) (PEDG-21) is a fully amorphous polycondensation product of diglycolic acid, ethylene glycol and diethylene glycol. When the two diols are used in excess, the resultant polycondensation product contains hydroxyl-capped end groups, and is then capable of serving as a macroinitiator in the subsequent, second stage ring-opening polymerization with a lactone monomer, such as lactide. The amount of polycondensation polyester used to prepare the copolyester of the present invention ranges from about 30 to 70% by weight based on the total weight of the copolyester. Suitable lactide monomers that may be reacted with the polycondensation polyester include, but are not limited to lactide (l, d, dl, meso) and combinations thereof. The preferred lactide monomer is l(−) lactide.

In another embodiment, the co-polyester of this invention may comprise the reaction product of a polycondensation polyester and a lactide composition further comprising active agents. Utilization of an active agent in combination with this invention depends on the desired benefit intended to be derived. For example, it may be advantageous to provide an implant comprising an co-polyester according to the invention that has at least one biologically active ingredient which can optionally be released locally after the implantation. Substances which are suitable as active agents may be naturally occurring or synthetic and include and are not limited to, for example, antibiotics, antimicrobials, antibacterials, antiseptics, chemotherapeutics, cytostatics, metastasis inhibitors, antidiabetics, antimycotics, gynaecological agents, urological agents, anti-allergic agents, sexual hormones, sexual hormone inhibitors, haemostyptics, hormones, peptide-hormones, antidepressants, vitamins such as Vitamin C, antihistamines, naked DNA, plasmid DNA, cationic DNA complexes, RNA, cell constituents, vaccines, cells occurring naturally in the body or genetically modified cells. The active agent may be present in an encapsulated form or in an adsorbed form. With such active agents, the patient diagnosis can be improved according to the application or a therapeutic effect can be achieved (e.g., better wound healing, or inflammation inhibition or reduction).

Preferred is the use of active agents as antibiotics that include such agents as gentamicin or ZEVTERA™ (ceftobiprole medocaril) brand antibiotic (available from Basilea Pharmaceutica Ltd., Basel Switzerland). Most preferred is the use of highly effective, broad band antimicrobials against different bacteria and yeast (even in the presence of bodily liquids) such as octenidine, octenidine dihydrochloride (available as active ingredient in Octenisept® disinfectant from Schülke & Mayr, Norderstedt, Germany as), polyhexamethylene biguanide (PHMB) (available as active ingredient in Lavasept® from Braun, Switzerland), triclosan, copper (Cu), silver (Ag), nanosilver, gold (Au), selenium (Se), gallium (Ga), taurolidine, N-chlorotaurine, alcohol based antiseptics such as Listerine® mouthwash, N α-lauryl-L-arginine ethyl ester (LAE), myristamidopropyl dimethylamine (MAPD, available as an active ingredient in SCHERCODINE™ M), oleamidopropyl dimethylamine (OAPD, available as an active ingredient in SCHERCODINE™ O), and stearamidopropyl dimethylamine (SAPD, available as an active ingredient in SCHERCODINE™ S), and most preferably octenidine dihydrochloride (hereinafter referred to as octenidine) and PHMB.

Also, depending on the active agent's solubility, a solvent system might be used to dissolve the inventive copolymer and the active agent as shown in Example 11. In this example, for the active agent, octenidine, a solvent mixture of acetone/ water was used for dip coating on mesh compositions. Of course other suitable solvent mixtures may be used such as those made from ethyl acetate/methanol mixtures or other solvents that the active agent(s) are soluble in.

Additionally, a contrast agent may be incorporated into the compositions of this invention. Such a contrast agent may be a biocompatible dye to create a visual marker as described in the EP1392198B1 or an agent such as a gas or gas creating substance for ultrasound contrast or MRI contrast, such as metal complexes like GdDTPA or superparamagnetic nanoparticles (Resovist™ or Endorem™) as taught in the EP 1324783 B1. X-Ray visible substances might be included as shown in the EP1251794B1 chosen from the following group: pure zirconium dioxide, stabilized zirconium dioxide, zirconium nitride, zirconium carbide, tantalum, tantalum pentoxide, barium sulphate, silver, silver iodide, gold, platinum, palladium, iridium, copper, ferric oxides, not very magnetic implant steels, non-magnetic implant steels, titanium, alkali iodides, iodated aromatics, iodated aliphatics, iodated oligomers, iodated polymers, alloys of substances thereof capable of being alloyed.

The compositions of this invention may be coated on medical devices or implants, and in some instances, comprise the substantially all of the material of the medical device or implant. Examples of suitable medical devices and implants include, but are not limited to sutures, tubes, vessel grafts, stents, dental implants, fabrics (wovens, non-wovens, embroidered), meshes, microspheres, fleeces, films, foams, wound dressings and pouches.

When the medical devices are not comprised substantially of the materials of this invention, the medical device being coated may comprise at least one substance selected from the group consisting of polyhydroxy acids, polylactides, polyglycolides, polyhydroxybutyrates, polyhydroxyvalerates, polycaprolactones, polydioxanones, synthetic and natural oligo- and polyamino acids, polyphosphazenes, polyanhydrides, polyorthoesters, polyphosphates, polyphosphonates, polyalcohols, polysaccharides, polyethers, polyamides, aliphatic polyesters, aromatic polyesters, natural polyamino acids, synthetic polyamino acids, genetically produced polyaminoacids, collagen, rh collagen, silk, pseudopolyaminoacids, polycyanoacrylates, polyethylene glycols, polyvinyl alcohols, derivatized cellulose, fats, waxes, fatty acids, fatty acid esters, polyphosphate esters, copolymers of polymerizable substances thereof, resorbable glasses, metals, alloys and combinations thereof. When the medical device is in the form of a mesh implants, preferred materials include at least one of the substance selected from the group consisting of polyalkenes, polypropylene, polyethylene, partially halogenated polyolefins, wholly halogenated polyolefins, fluorinated polyolefins, polytetrafluorethylene, polyvinylidene fluoride, polyisoprenes, polystyrenes, polysilicones, polycarbonates, polyarylether ketones, polymethacrylic acid esters, polyacrylic acid esters, polyimides, copolymers of polymerizable substances and mixtures thereof.

Conventional techniques may be used to apply materials of this invention on medical devices and implants and include, but not limited to, dip coating, spraying, inkjet (solvent jet) application, swelling, powder coating with sintering, injection molding, and plasma or laser deposition coating.

Preferably the application of the compositions of this invention will form coatings comprising from about 1000 ppm (0.1 weight %) to about 200,000 ppm (20 weight %), most preferably from about 8000 ppm (0.8 weight %) to about 20,000 ppm (2.0 weight %) of the implant.

Example 1

Synthesis of Hydroxy Terminated Poly(ethylene diglycolate) (PEDG)

A twin-agitated reactor with intermeshing HELICONE patterned blades (Atlantic 10CV reactor) was employed. After charging the reactor with 10.0 kg of diglycolic acid, 13.9 kg of ethylene glycol (EG) and 1.86 grams of dibutyltin oxide catalyst, the pressure was reduced to below 1 Torr and the vacuum preserved overnight. The next day the vacuum was released with dry nitrogen (argon can be substituted) and the heating of mixture started. When the reactor temperature reached 150° C., an agitator speed was set to 30 RPM. Soon first distillate appeared containing mostly water, an esterification by-product. The reaction was continued at 165° C. for a couple of more hours until approximately all water was distilled and/or first traces of EG appeared in the distillate. After the first nitrogen/argon stage was completed, pressure was lowered gradually to full vacuum in steps while the temperature of the batch was maintained at 165° C. A vacuum of about 30-50 mTorr was maintained throughout the rest of the reaction. Melt and solution viscosities were regularly checked to ensure a polymer of a desired molecular weight. A hydroxy end-capped polymer was discharged in portions at different of reaction time under vacuum. The longer the reaction time, the higher is molecular weight of the material. The product is a fully amorphous, colorless viscous liquid. The inherent viscosities (IV) of discharged PEDG prepolymers ranges from about 0.30 to about 0.40 dL/g, which corresponds to weight average molecular weights of about 5,000 to 10,000 g/mol.

Example 2

The Copolymerization of Hydroxy Terminated Poly(ethylene diglycolate) with a L(−)-lactide, (PLLA): Copolymer Composition (PEDG/PLLA 40/60 Wt. %)

A portion of the Poly(ethylene diglycolate) made in Example 1 (36.0 g) with IV=0.37 dL/g was added into an oven dried 250 milliliter round bottom flask. In the nitrogen glove box, the L(−)-lactide (54.0 g) and catalyst, Stannous Octoate (0.019 ml) were charged. A mechanical stirrer, nitrogen adapter and stirrer bearing were added to the 250 ml flask's neck opening. The vessel was pulled under a vacuum of less than 500 mTorr at room temperature and held overnight. The polymer was reacted using a stepped temperature profile. The next day the flask was released to nitrogen and placed in the oil bath. The bath temperature was set to 190° C. without agitation. Once the temperature reached approximately 110° C. the mechanical stirrer was set at 4 RPM. When the melt appeared homogenous and clear at about 170° C., the agitation was reduced to 2 RPM. The reaction was hold at 190° C. for about 5 hours. After 5 hours, the reaction was stopped and allowed to cool overnight under nitrogen.

All the glass inserts were removed from the flask, leaving only the mechanical stirrer, polymer resin and the round bottom flask. The flask was then wrapped in aluminium foil and the polymer product was removed from the reaction flask through liquid nitrogen quenching. The remaining glass shards were ground/sanded off of the polymer product. The polymer fragments were collected and placed in a Teflon coated pan. The pan was placed in the vacuum oven and pulled under vacuum overnight. The next day the vacuum oven was set to 110° C. and the polymer was devolitized for 16 hours. The polymer conversion was 98.5%. At room temperature the copolymer is a light yellowish fully amorphous solid, with the softening point, as determined by Fisher-Johns method, of 98° C. The weight average molecular weight, Mw is 25,900 g/mol, and IV 0.65 dL/g.

Example 3

The Copolymerization of Hydroxy Terminated Poly(ethylene diglycolate) with a L(−)-lactide, (PLLA): Copolymer Composition (PEDG/PLLA 50/50 Wt. %)

A portion of the poly(ethylene diglycolate) made in Example 1 (50.0 g) with IV=0.37 dL/g was added into an oven dried 250 milliliter round bottom flask. In the nitrogen glove box, the L(−)-lactide (50.0 g) and catalyst, Stannous Octoate (0.018 ml) were charged. Polymerization procedure was identical to that described in Example 2.

The final polymer conversion was calculated to be 97.4%. At room temperature the copolymer is a light yellowish fully amorphous solid, with the softening point, as determined by Fisher-Johns method, of 83° C. The weight average molecular weight, Mw is 24,000 g/mol, and IV 0.53 dL/g.

Example 4

The Copolymerization of Hydroxy Terminated Poly(ethylene diglycolate) with a L(−)-lactide, (PLLA): Copolymer Composition (PEDG/PLLA 60/40 Wt. %)

A portion of the poly(ethylene diglycolate) made in Example 1 (60.0 g) with IV=0.37 dL/g was added into an oven dried 250 milliliter round bottom flask. In the nitrogen glove box, the L(−)-lactide (40.0 g) and catalyst, Stannous Octoate (0.014 ml) were charged. Polymerization procedure was identical to that described in Example 2.

The final polymer conversion was calculated to be 98.0%. At room temperature the copolymer is a light yellowish fully amorphous solid, with the softening point, as determined by Fisher-Johns method, of 81° C. The weight average molecular weight, Mw is 18,500 g/mol, and IV 0.45 dL/g.

Example 5A

The Copolymerization of Hydroxy Terminated Poly(ethylene diglycolate) with a L(−)-lactide, (PLLA): Copolymer Composition (PEDG/PLLA 60/40 Wt. %)

A portion of the poly(ethylene diglycolate) made in Example 1 (60.0 g) with IV=0.41 dL/g was added into an oven dried 250 milliliter round bottom flask. In the nitrogen glove box, the L(−)-lactide (40.0 g) and catalyst, Stannous Octoate (0.014 ml) were charged. Polymerization procedure was as described in Example 2.

The final polymer conversion was calculated to be 99.0%. At room temperature the copolymer is a light yellowish fully amorphous solid. The weight average molecular weight, Mw is 16,800 g/mol, and IV 0.50 dL/g. The residual L(−)-lactide monomer in the dried resin was 0.6 wt. %.

Example 5B

The Copolymerization of Hydroxy Terminated Poly(ethylene diglycolate) with a L(−)-lactide, (PLLA): Copolymer Composition (PEDG/PLLA 60/40 wt. %)

A portion of the poly(ethylene diglycolate) made in Example 1 (60.0 g) with IV=0.31 dL/g was added into an oven dried 250 milliliter round bottom flask. In the nitrogen glove box, the L(−)-lactide (40.0 g) and catalyst, Stannous Octoate (0.014 ml) were charged. Polymerization procedure was as described in Example 2.

The final polymer conversion was calculated to be 97.3%. At room temperature the copolymer is a light yellowish fully amorphous solid. The weight average molecular weight, Mw is 11,200 g/mol, and IV 0.37 dL/g. The residual L(−)-lactide monomer in the dried resin was 0.4 wt. %.

Example 6

Dissolution Study in Various Organic Solvents

PEDG/PLLA copolymers described in this study were found to be readily soluble in acetone and soluble, but with difficulty in some embodiments, in ethyl acetate, ethyl lactate, N-methyl pyrolidone and benzyl alcohol (i.e., sometimes requiring 18-24 hours to fully dissolve at room temperature). The PEDG/PLLA copolymers are essentially insoluble in benzyl benzoate. It has also been observed that as the PLLA component is increased relative to the PEDG component, the ease of solubility has also increased. Also, in instances where micro dispersion of the PEDG/PLLA copolymer had formed in an organic solvent, such as described in Example 4 below, adequate coating solutions were still achieved.

Example 7

Physical Characterization of PEDG/PLLA Copolymers

In order to examine physical characteristics of copolymers described in Examples 2-4, several 5-mil (0.13 millimeters) films were compression molded using a hot press available from Tetrahedron (MTP-14 Tetrahedron™ Compression Molding press). The results from variety of physical tests are summarized in Table 1.

TABLE 1

Selected physical properties of PEDG/PLLA films

| Polymer films | Mw/IV | WAXD Cryst (%) | Tg/Tm (° C.) | Load at Peak (lbf) | Load at Break (lbs) | % Strain at break | Young's modulus (ksi) | Spread. Angle[1] (Δ°) | Abs.[2] rate, $t_{1/2}$ (hours) |
|---|---|---|---|---|---|---|---|---|---|
| Example 2 | 26k/0.65 | 0 | 28.5/NA | 4.42 | 4.42 | 5.6 | 120 | 63 | 22 |
| Example 3 | 24k/0.54 | 0 | 19.5/NA | 1.36 | 1.05 | 709 | 49 | 65 | 14 |
| Example 4 | 19k/0.45 | 0 | 15.0/NA | 0.24 | 0.18 | 1476 | 4.7 | 70 | 9 |

Comments:

[1] Spreading angle is a measure of how fast the drop of water is absorbed by the polymer. Higher numbers suggest faster diffusion of water into the bulk.

[2] Data for hydrolysis profile are obtained from automated hydrolysis unit at 75° C. in deionized water, pH = 7.3 with 0.05N NaOH.

Referring to Table 1, the films made from copolymers with a higher PEDG content show lower glass transition temperature, Tg, weaker tensile strength and modulus but exhibit much higher elongation. Furthermore, increasing the level of PEDG increases the surface and bulk hydrophilicity of the films, as measured by contact angle measurements and hydrolysis experiments, respectively.

Example 8

In-Vitro Bacterial Attachment Examination

Coating Procedures:

5 mil PROLENE® polypropylene meshes (Ethicon, Inc.) were cut into 10 cm×3 m stripes and pulled through a coating bath at a speed of about 3 mm/s containing 1.5% (w/w) of each coating compound in ethyl acetate, air dried and cut to desired size and sterilized with ethylene oxide. Samples labelled 71-1 and 71-2 using the copolymer described in the Example 4 formed a micro dispersion in ethyl acetate. The sample labelled 71-3 coated with copolymer described in the Example 2 formed a clear solution in ethyl acetate.

Short Term Bacterial Attachment Test—20 Minutes

This test was performed for 20 minutes: the first 10 minutes consisted of pre-incubation of the test samples in blood plasma and the subsequent 10 minutes consisted of bacterial attachment in phosphate buffered saline (PBS) which provides good indication for early bacterial attachment. Since with triclosan there is a lag time (referred to as 'time-to-kill'), it is beneficial to complement this with something that will reduce bacterial attachment at prior to the 'time-to-kill' duration. Loosely attached bacteria were removed from the samples by rinsing 3 times with a solution of Tween/Lecitin. The remaining attached bacteria were removed by ultrasonic treatment. The number of bacteria was counted by an agar plate count.

Table 2 and FIG. 1 show the results of the bacterial attachment test. Surprisingly, the PEDG/PLLA coated samples of this invention reduced the bacterial attachment more than potent inhibitors like triclosan, or triclosan in combination with Triton X-100 and Lutron F68. Additionally, the antimicrobial activity of agents is increased as shown in blood agar transfer experiments.

Example 9

Long Term Attachment Assay (24 hour) S. Aureus on Polymer Coated and Uncoated Glycolide/ε-Caprolactone Films in the Presence of Proteins (FCS)

Resin made from a copolymer from glycolide and ε-caprolactone (75/25 mole %) was extruded into 50 μm films. Such films in the range from 10-100 μm are useful as adhesion barrier to prevent intestinal adhesion and could be also assemble to a surgical mesh useful as adhesion barrier surgical mesh. Also an about 100 nm Glycolide/ε-caprolactone film is used as a reinforcing member in the Ultrapro Hernia System™.

The glycolide/ε-caprolactone film was dip coated in a 1% (w/w) solution of Example 5A and Example 5B in acetone with an incubation time of 2 minutes and a draw speed of about 3 mm/s Samples, were dried for 15 minutes, stored in vacuum, cut into disks of 2 cm diameter and sterilized using ethylene oxide and packaged dried in an aluminium blister used for sutures. No non-homogenicity was observed under the light microscope.

Figure 2:
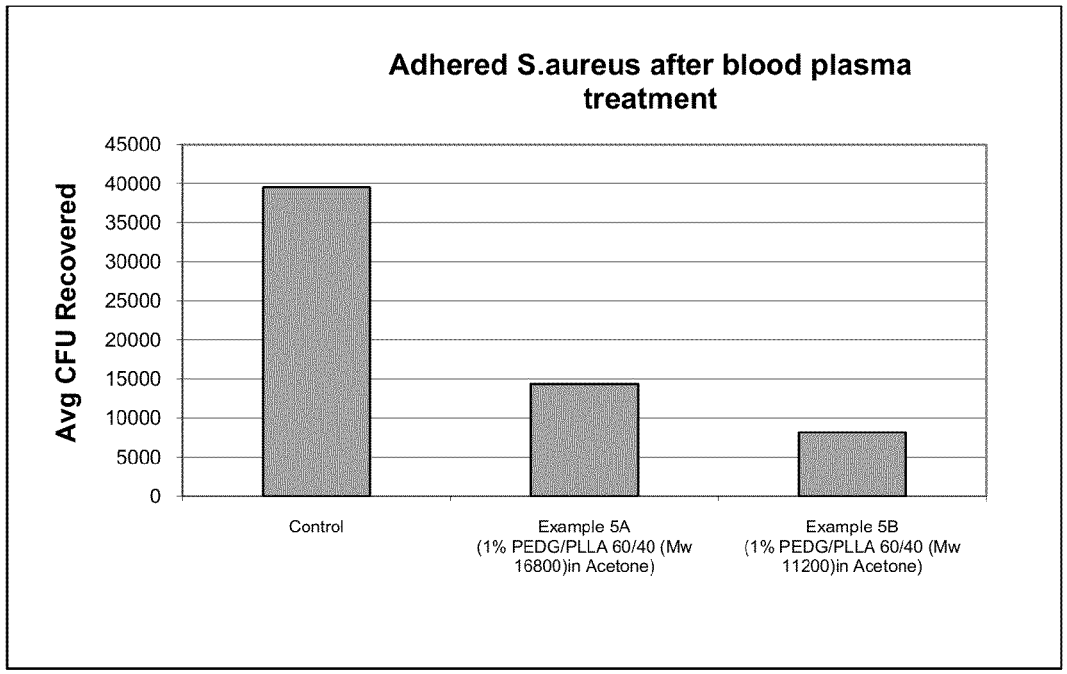
FIG. 2 demonstrates a reduction of bacterial attachment of the compositions of this invention compared with a control in a 24 hour incubation study.

Samples were inoculated in 2 ml 1E6/ml S. aureus medium containing tryptic soy broth (TSB), saline and 20% heat deactivated sterile filtrated fetal calf serum (FCS) for 24 h, 37° C. in a shaker. Loosely attached bacteria were removed from the samples by rinsing 3 times with a solution of Tween/Lecitin. The remaining attached bacteria were removed by ultrasonic treatment. The number of bacteria was counted by an agar plate count. Referring to Table 3, one sees the CFU adhesion reduction benefits of 64% and 79% for films coated with the compositions of Examples 5A and 5B, respectively, compared with the uncoated mesh (control). These results are graphically depicted in FIG. 2.

TABLE 2

Reduction of S. Aureus adhesion in the presence of proteins (FCS) on coated and uncoated 5 mil Prolene ® polypropylene mesh

| sample # | treatment | % additive | avg CFU recovered | std dev | avg % recovered | std dev |
| --- | --- | --- | --- | --- | --- | --- |
| 3400-45-G3 | Untreated mesh | 0 | 1.55E+05 | 1.77E+04 | 0.2713 | 0.0311 |
| 3400-58-1 | TRICLOSAN | 1.5 | 5.08E+04 | 2.28E+04 | 0.0892 | 0.0400 |
|  | TRICLOSAN + TX100 | 1.5 1.5 | 3.22E+04 | 5.35E+03 | 0.0564 | 0.0094 |
| 3400-58-4 | TRICLOSAN + Lutrol F68 | 1.5 1.5 | 4.13E+04 | 1.24E+04 | 0.0725 | 0.0217 |
| 3400-71-1 | PEDG/PLLA 60/40 (Example 4) | 1.5 | 2.50E+04 | 3.61E+03 | 0.0439 | 0.0063 |
| 3400-71-2 | TRICLOSAN + PEDG/PLLA 60:40 (Example 4) | 1.5 1.5 | 2.22E+04 | 1.73E+03 | 0.0389 | 0.0030 |

Inoculums: 2.85E+06 colony-forming units (CFU)/ml
Total CFU: 5.70E+07

TABLE 3

Reduction of Bacterial *S. Aureus* on 50 μm glycolide and ε-caprolactone film and glycolide and ε-caprolactone films coated with Samples 5A and 5B in the presence of plasma proteins

| Sample | Coating solution | avg CFU/film | % CFU adhesion reduction |
|---|---|---|---|
| Glycolide/ε-caprolactone Film (control) | uncoated | 39500 | 0% |
| Film + 1% Example 5A | 1% PEDG/PLLA 60/40 (Mw 16,800) in Acetone | 14333 | 64% |
| Film + 1% Example 5B | 1% PEDG/PLLA 60/40 (Mw 11,200) in Acetone | 8166 | 79% |

Example 10

Zone of Inhibition Testing

Sterilized samples from Example 8 were tested in a Zone of Inhibition (ZOI) test containing sheep blood agar. Samples were transferred after every 24 hours into a fresh plate. All triclosan coated meshes showed a sustained action over 3 days.

Figure 3:
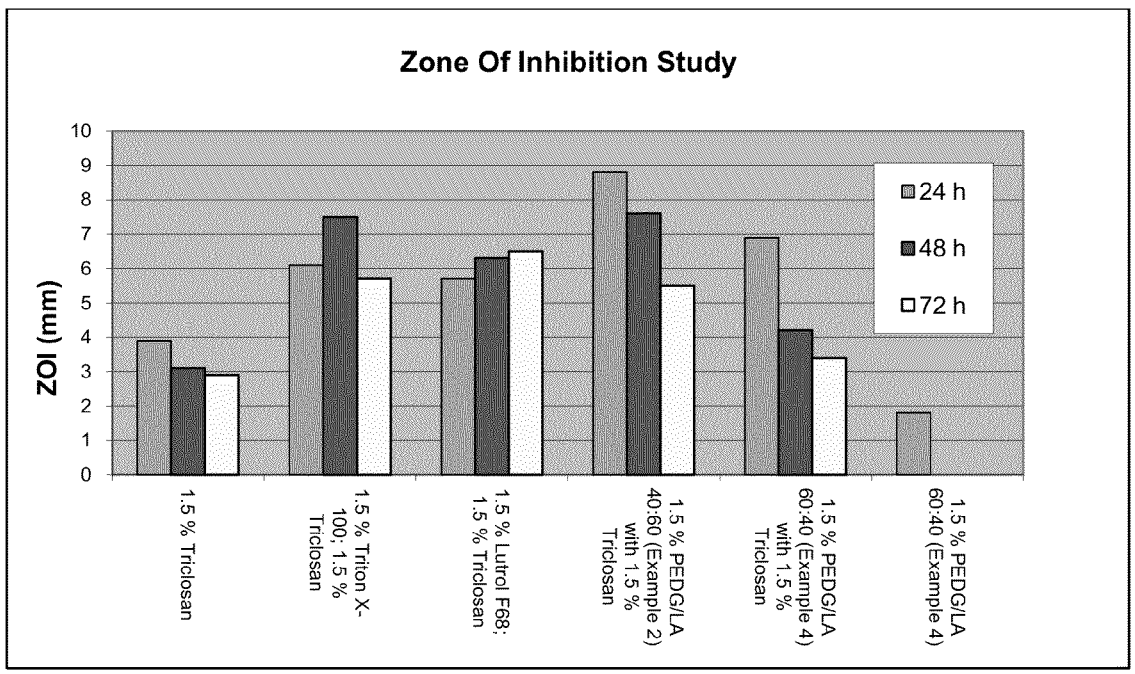
FIG. 3 depicts the antimicrobial zone of inhibition results for compositions of this invention compared with other materials at intervals of 24, 48 and 72 hours.

Results of the ZOI testing are reported in Table 4 and depicted in FIG. 3. Referring to FIG. 3, all polymer coated or surfactant coated meshes with triclosan, showed increased ZOI's in the blood agar, compared to just triclosan coated meshes. Whereby meshes coated with Example 2 of this invention, showed the biggest ZOI over 2 days. The sample coated just with the inventive polymer without triclosan showed a slight bacteriostatic action in the 24 hour test, resulting in a ZOI of 1.8 mm.

TABLE 4

| | | Zone of inhibition (mm) | | |
|---|---|---|---|---|
| label | treatment | 24 h | 48 h | 72 h |
| 3400-58-1 | 1.5% Triton X-100 1.5% Triclosan | 6.1 | 7.5 | 5.7 |
| 3400-58-4 | 1.5% Lutrol F68 1.5% Triclosan | 5.7 | 6.3 | 6.5 |
| 3400-71-1 | 1.5% PEDG/PLLA 60:40 (Example 4) | 1.8 | 0 | 0 |
| 3400-71-2 | 1.5% PEDG/PLLA 60:40 (Example 4) 1.5% Triclosan | 6.9 | 4.2 | 3.4 |
| 3400-71-3 | 1.5% PEDG/PLLA 40:60 (Example 2) 1.5% Triclosan | 8.8 | 7.6 | 5.5 |
| 3400-45-63 | 1.5% Triclosan | 3.9 | 3.1 | 2.9 |

Example 11

In-Vivo, 7 Days Rat Infection Study with *E. Coli*

Control: Mesh-Laminate (AB119)

A lightweight surgical 3.5 mil polypropylene-mesh having the Ultrapro® mesh structure was heat laminated between 20 μm glycolide/ε-caprolactone films using an 8 μm poly(p-dioxanone), (PDS) film as a melt glue. Round 1.5 cm disks were punched out and the implant was packaged and sterilized using ethylene oxide.

Test-Article: Mesh-Laminate with 1600 ppm Octenidine Dispersed in PEDG/PLLA Matrix The described mesh-laminate, AB119 was dip coated in a solution of 0.1% octenidine hydrochloride and 0.9% 60/40 PEDG/PLLA copolymer (Example 5B, AB112) (w/w) in Water/Acetone 10%/90% (w/w), air dried and vacuum dried. The mesh and the films are impregnated in this coating. The total of 1600 ppm octenidine were determined to have been deposited on the implant.

Round 1.5 cm diameter disk-shaped implants (of the test and control implants) were implanted subcutaneously into Young male Sprague-Dawley rats (weight 300 gm-400 gm) and challenged with 1 E5 CFU's of *Escherichia coli* (strain ATCC 25922). After 7 days, the bacteria on the implant and in the surrounding tissue were measured.

Table 5 shows the results on the mesh and in the surrounding tissue. The mesh coated with the 60/40 PEDG/PLLA/octenidine coating resulted in a significant reduction of bacteria of more than 5 log (99.999%).

TABLE 5

Log Average CFU's for either Mesh or Tissue biopsy samples.

| | *E. Coli* on mesh Average Log CFU/mesh | SD | *E. Coli* in Tissue Average Log CFU/g | SD |
|---|---|---|---|---|
| Control Mesh (AB119) | 7.05 | 0.36 | 7.41 | 0.44 |
| Mesh + Octenidine + Example 5B (AB112) | 0.66 | 0.66 | 2.08 | 2.44 |
| | P < 0.0000 | | P < 0.0003 | |

Example 12

In-Vivo, 7 Days Rat Infection Study with *S. Aureus*

The same test as described in Example 11 was performed using *Staphylococcus aureus* (CBE 71) with an inoculum of 1 E7 bacteria per implant.

The sample containing PEDG/PLLA copolymer (Example 5B) coating on the mesh (AB74, Table 6) resulted a reduction after one week implantation of about 80% compared to the control (polypropylene mesh).

The mesh sample containing a coating of Example 5B copolymer and octenidine (AB 112, Table 2) showed a sterile mesh after a one week implantation. No surviving bacteria on the mesh or in the surrounding tissue were found.

TABLE 6

Average CFU's of *S. aureus* for Mesh samples after 7 days rat implantation.

| Sample | Average CFU/half mesh | Reduction (%) |
|---|---|---|
| AB119 (Control mesh) | 1.0E+06 | 0 |
| AB74 (Mesh + Example 5B) | 1.6E+05 | 80 |
| AB112 (Mesh + Example 5B + Octenidine) | 0.0E+00 | Sterile |

As a further non comparative example, a two week in vivo rat study was conducted to investigate the efficacy of a 1700 ppm octenidine coating on a glycolide-caprolactone copolymer mesh laminate. The results showed a count of only 10-100 bacteria per implant at the conclusion of the study. Further comparative examples are needed to investigate the effect of combination of the compositions of this invention with octenidine to establish any beneficial effect due to the presence of the compositions of this invention in a two week in vivo rat study.

Example 13

Solubility in Non-Toxic Solvents

This example demonstrates the solubility of compositions of this invention in the acetone. As a note, octenidine in combination with the polymeric compositions of this invention were shown to be soluble in acetone/water (90/10) mixtures. (i.e., acetone to keep the inventive polymers in solution and water to keep the octenidine in solution).

Figure 4:
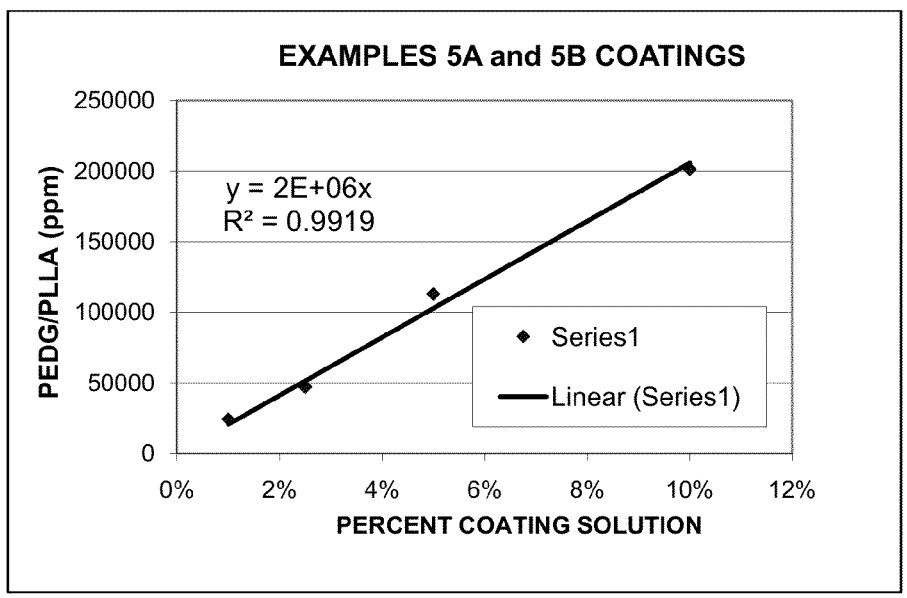
FIG. 4 demonstrates that the compositions of this invention are capable of coatings upward and over of 20 wt/wt % on an implant.

The compositions of Example 5A and 5B were coated on a composite of a polypropylene mesh laminated between 20 μm glycolide-caprolactone films. The results provided in Table 7 (and depicted in FIG. 4) show that the embodiments of the compositions of this invention solubilized in acetone are capable of loading up to and over ~200000 ppm (20% w/w) on the mesh after drying.

TABLE 7

PEDG/PLLA Coating Levels on Implants

| | Coating Solution %(w/w) | ppm on implant |
|---|---|---|
| Example 5A | 1% | 24303 |
| Example 5B | 1% | 21125 |
| Example 5A | 2.50% | 47049 |
| Example 5B | 2.50% | 49033 |
| Example 5A | 5% | 112920 |
| Example 5B | 5% | 98585 |
| Example 5A | 10% | 201364 |
| Example 5B | 10% | 205224 |

Although this invention has been shown and described with respect to detailed embodiments thereof, it will understood by those skilled in the art that various changes in form and detail thereof may be made without departing from the spirit and scope of the claimed invention.

What is claimed is:

1. An implantable medical device comprising a coating of a composition comprising an antimicrobial linear amorphous co-polyester comprising the reaction product of a polycondensation polyester and a lactide-rich monomer composition, wherein the polycondensation polyester comprises linear polyethylene diglycolate; wherein the co-polyester comprises about 40 to 60% by weight of the polycondensation polyester based on the total weight of the co-polyester and comprises an average molecular weight of about 10,000 to about 20,000 g/mol and is soluble in a non-toxic organic solvent; and wherein the coating comprises from about 0.1 weight % to about 20 weight % of the implantable medical device.

2. The medical device of claim 1, wherein the co-polyester comprises about 50% by weight of the polycondensation polyester based on the total weight of the co-polyester.

3. The medical device of claim 1, wherein the average molecular weight of polycondensation polyester comprises an average molecular weight of about 2,000 to 10,000 g/mol.

4. The medical device of claim 1, further comprising an active agent.

5. The medical device of claim 4, wherein the active agent is selected form the group consisting of natural ingredients, synthetic ingredients, antibiotics, chemotherapeutics, cytostatics, metastasis inhibitors, antidiabetics, antimycotics, antimicrobials, antibacterials, vitamins, gynaecological agents, urological agents, anti-allergic agents, sexual hormones, sexual hormone inhibitors, haemostyptics, hormones, peptide hormones, vitamins, antidepressants, anti-histamines, naked DNA, plasmid DNA, cationic DNA complexes, RNA, cell constituents, vaccines, cells occurring naturally in the body, genetically modified cells and mixtures thereof.

6. The medical device of claim 5, wherein the active agent is an antimicrobial selected from the group consisting of octenidine, PHMB, triclosan, copper, silver, nanosilver, gold, selenium, gallium, taurolidine, N-chlorotaurine, alcohol, LAE, MAPD, OAPD, and mixtures thereof.

7. The medical device of claim 6, wherein the antimicrobial is triclosan.

8. The medical device of claim 6, wherein the antimicrobial is octenidine.

9. The medical device of claim 6, wherein the antimicrobial is PHMB.

10. The medical device of claim 1, wherein the lactide-rich composition comprises more than 50 weight percent (l,d,dl, meso) lactide monomers and the remaining constituents comprise at least one constituent selected from the group consisting of glycolides, p-dioxanones, trimethylene carbonates, tetramethylene carbonates, epsilon-caprolactones, delta-valerolactones, beta-butyrolactones, epsilon-decalactones, 2,5-diketomorpholines, pivalolactones, alpha,alpha-diethyl-propiolactones, ethylene carbonates, ethylene oxalates, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one, and combinations thereof.

11. The medical device of claim 1, wherein the medical device is selected from the group consisting of sutures, tubes, vessel grafts, stents dental implants, fabrics, meshes, microspheres, fleeces, films, foams, non-wovens, wovens, wound dressings, pouches, embroidered fabrics and combinations thereof.

12. The medical device of claim 1, wherein the non-toxic solvent is selected form the group consisting of ethanol, 2-propanol, ethyl acetate, acetone, methyl ethyl ketone (MEK) and mixtures thereof.

13. An antimicrobial adhesion barrier comprising a linear amorphous co-polyester comprising the reaction product of a polycondensation polyester and a lactide-rich monomer composition, wherein the polycondensation polyester comprises linear polyethylene diglycolate; wherein the co-polyester comprises about 40 to 60% by weight of the polycondensation polyester based on the total weight of the co-polyester and comprises an average molecular weight of about 10,000 to about 20,000 g/mol and is soluble in a non-toxic organic solvent.

* * * * *